United States Patent [19] [11] 4,185,989
Houbion et al. [45] Jan. 29, 1980

[54] 3-PHENACYL PHTHALDIDE SAFENING AGENTS

[75] Inventors: John A. Houbion, Kirkwood; David E. Schafer, Creve Coeur, both of Mo.

[73] Assignee: Monsanto Company, St. Louis, Mo.

[21] Appl. No.: 929,132

[22] Filed: Jul. 28, 1978

[51] Int. Cl.$^2$ .......................... A01N 9/00; A01N 9/20
[52] U.S. Cl. .......................................... 71/88; 71/100; 71/118; 71/121
[58] Field of Search ................................... 71/88, 118

[56] References Cited

U.S. PATENT DOCUMENTS

| | | | |
|---|---|---|---|
| 3,407,206 | 10/1968 | Bousquet | 260/310 |
| 3,442,945 | 5/1969 | Olin | 71/118 |
| 3,564,768 | 2/1971 | Hoffmann | 71/100 |
| 3,574,746 | 4/1971 | Chupp | 71/118 |
| 3,702,759 | 11/1972 | Hoffmann | 71/77 |
| 3,719,466 | 3/1973 | Ahle | 71/88 |
| 3,989,503 | 11/1976 | Pallos et al. | 71/100 |
| 4,021,224 | 5/1977 | Pallos et al. | 71/100 |
| 4,033,756 | 7/1977 | Hoffmann | 71/100 |

OTHER PUBLICATIONS

Bousquet et al., "Synthesis of 3,3a-Dihydro-8H-etc.," (1974) J. Org. Chem. 40, pp. 2208-2211 (1975).
Brown et al., "The Effect of Root Geotropism etc.," (1973) Pest. Sci. 4, pp. 473-484 (1973).

Primary Examiner—Glennon H. Hollrah
Attorney, Agent, or Firm—Arnold H. Cole; Donald W. Peterson

[57] ABSTRACT

Certain 3-phenacyl phthalides have been found useful as safening agents to reduce herbicidal injury to rice plants.

55 Claims, No Drawings

3-PHENACYL PHTHALDIDE SAFENING AGENTS

This invention relates to compositions containing a herbicide and a safening agent therefor, and to methods of using such compositions to reduce herbicidal injury to treated crop plants. More particularly, this invention is concerned with novel compositions which comprise a known herbicide and a 3-phenacyl phthalide. The invention is also concerned with the methods of treating rice plants, rice seeds, or the plant growth medium, with such novel compositions to prevent or reduce the injury to the rice plants which would otherwise occur due to use of the herbicide alone.

BACKGROUND OF THE INVENTION

Butachlor is the common name for the active herbicide ingredient 2-chloro-2',6'-diethyl-N-(butoxymethyl)acetanilide. The preparation and use of this compound to control the growth of undesired plants is described in U.S. Pat. No. 3,442,945. Other active herbicide ingredients described in this patent include 2-chloro-2'-tert. butyl-6'-methylacetanilide and 2-chloro-2'-tert. butyl-6'-methyl-N-(butoxymethyl)acetanilide. U.S. Pat. No. 3,574,746 describes the preparation and use of the active herbicide ingredient N-(2-butoxyethyl)-N-(2,6-dimethyl-1-cyclohexen-1-yl)-α-chloroacetamide.

Molinate is the common name for the active herbicide ingredient S-ethyl hexahydro-1H-azepine-1-carbothiolate, whose preparation and use is described in U.S. Pat. No. 3,198,786. Benthiocarb is the common name for the active herbicide ingredient S-(4-chlorobenzyl)N,N-diethylthiolcarbamate, whose preparation and use is described in U.S. Pat. No. 3,632,332. Butralin is the common name for the active herbicide ingredient N-sec. butyl-4'-tert. butyl-2',6'-dinitroaniline, whose preparation and use is described in U.S. Pat. No. 3,672,866.

In the treatment of rice, it is often desirable to use relatively high rates of the active herbicide ingredient to achieve more rapid or more complete control of the undesired grasses which compete with the crop. Such higher rates, however, can create a significant problem because of the increased level of the detrimental herbicidal effect on the rice crop.

The effect of 3-phenacyl phthalide on root geotropism in various plants is discussed in the literature. Tests of this compound on cress and ryegrass are described in Pesticide Science, Vol. 4, pgs. 473–84 (1973).

DESCRIPTION OF THE INVENTION

In accordance with the present invention, it has been found that herbicidal injury to the rice plants can be prevented or reduced in magnitude by applying the above-named herbicides in conjunction with certain 3-phenacyl phthalides which serve as safening agents.

The 3-phenacyl phthalides which are employed in the practice of this invention have the formula

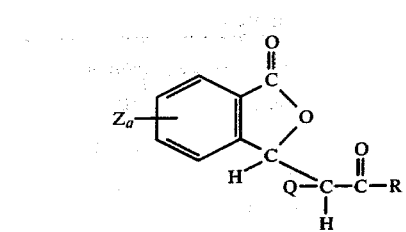

wherein: R is selected from phenyl, α-naphthyl, cyclohexyl, dichlorophenyl provided that the chloro substituents are not on adjacent carbon atoms, trichlorophenyl, di(lower alkyl)phenyl, tri(lower alkyl)phenyl, di(lower alkoxy) phenyl provided that at least one meta position is unsubstituted,

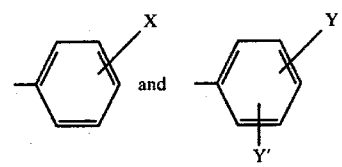

where X is lower alkyl, lower alkoxy, chloro, fluoro, iodo, trifluoromethyl, hydroxy, amino or 3'-nitro, and Y and Y' are unlike and are hydroxy, methyl or lower alkoy; a is zero or one; Z is selected from 5, 6 or 7-chloro, 6-nitro and methoxy provided that when Z is 4-methoxy, R must be a substituted phenyl; and Q is hydrogen or bromo provided that when Q is bromo at least one of X, Y, Y' or Z must be lower alkoxy. It will be recognized that the compounds of this formula contain an asymetric carbon atom and hence may exist in two stereoisomeric forms. Both of such forms, together with mixtures thereof, are contemplated within the scope of this invention.

As employed herein, the term "lower" designates those straight or branched chain radicals having up to four carbon atoms. The above-described compounds can be prepared by methods known in the prior art. Such methods are described in U.S. Pat. No. 3,407,206, and in Journal of Organic Chemistry, Vol. 40, pgs. 2208–11 (1975).

Representative examples of the compounds within the scope of the above formula include:

|     |                                          | m.p. ° C.   |
|-----|------------------------------------------|-------------|
| 1.  | 3',4'-dimethoxy-3-phenacyl phthalide     | 146–147     |
| 2.  | 2'-chloro-3-phenacyl phthalide           | 91–92       |
| 3.  | 3'-methoxy-3-phenacyl phthalide          | 181.5–182.5 |
| 4.  | α-bromo-2'-methoxy-3-phenacyl phthalide  | 115         |
| 5.  | 4'-methoxy-3-phenacyl phthalide          | 114         |
| 6.  | 4'-chloro-3-phenacyl phthalide           | 135–136     |
| 7.  | 2',5'-dimethoxy-3-phenacyl phthalide     | 124–125     |
| 8.  | α-bromo-3',-methoxy-3-phenacyl phthalide | 72–73       |
| 9.  | 3'-trifluoromethyl-3-phenacyl phthalide  | 121–122     |
| 10. | 4'-methyl-3-phenacyl phthalide           | 145–146     |
| 11. | 2'-methoxy-3-phenacyl phthalide          | 125         |
| 12. | α-bromo-3',4'-dimethoxy-3-phenacyl phthalide | 201–202 |
| 13  | 3-methyl-3-phenacyl phthalide            | 104–105     |
| 14. | 2'-fluoro-3-phenacyl phthalide           | 114         |
| 15  | 3'-nitro-3-phenacyl phthalide            | 161–162     |
| 16. | 3-phenacyl phthalide                     | 141–142     |
| 17. | 2',5'-dichloro-3-phenacyl                |             |

-continued

| | | m.p. ° C. |
|---|---|---|
| | phthalide | 121–123 |
| 18. | 4'-hydroxy-3-phenacyl phthalide | >280 |
| 19. | 2',4',6'-trimethyl-3-phenacyl phthalide | 138–140 |
| 20. | 2',4'-dimethoxy-3-phenacyl phthalide | 142–143 |
| 21. | 4'-fluoro-3-phenacyl phthalide | 129–131 |
| 22. | 3-(α-naphthoylmethyl)phthalide | 145–148 |
| 23. | 2'-amino-3-phenacyl phthalide | 158–159 |
| 24. | 4'-amino-3-phenacyl phthalide | 189 |
| 25. | 6-methoxy-3-phenacyl phthalide | 144–145 |
| 26. | 5-methoxy-3-phenacyl phthalide | 126 |
| 27. | 5-chloro-3-phenacyl phthalide | 184 |
| 28. | 6-nitro-3-phenacyl phthalide | 153 |
| 29 | 7-chloro-3-phenacyl phthalide | 134–135 |
| 30. | 2'-iodo-3-phenacyl phthalide | 84–85 |
| 31. | 2',5,5'-trimethoxy-3-phenacyl phthalide | 130 |
| 32. | 2',4,5'-trimethoxy-3-phenacyl phthalide | 131 |
| 33. | α-bromo-2',4,5'-trimethoxy-3-phenacyl phthalide | 188 |
| 34. | 4'-butoxy-3-phenacyl phthalide | 95 |
| 35. | 4'-butyl-3-phenacyl phthalide | 111–112 |
| 36. | 2'-ethoxy-5'-methoxy-3-phenacyl phthalide | 111 |
| 37. | 2',5'-dimethyl-3-phenacyl phthalide | 122 |
| 38. | 2',5'-diethyl-3-phenacyl phthalide | 47 |
| 39. | 2'-methoxy-5'-methyl-3-phenacyl phthalide | 134 |
| 40. | 2'-hydroxy-5'-methyl-3-phenacyl phthalide | 132 |
| 41. | 2'-propoxy-5'-methyl-3-phenacyl phthalide | 105 |
| 42. | α-bromo-4-methoxy-3-phenacyl phthalide | 149–151 |
| 43. | 2',3',4'-trichloro-3-phenacyl phthalide | 142–143 |
| 44. | 5-chloro-2',5'-dimethoxy-3-phenacyl phthalide | 174–175 |
| 45. | 2'-trifluoromethyl-3-phenacyl phthalide | 109 |
| 46. | 6-chloro-3-phenacyl phthalide | 161–162 |
| 47. | 2',5'-diethoxy-3-phenacy phthalide | 87–88 |
| 48. | 3-cyclohexylcarbonylmethyl phthalide | 89 |

The safening agents of this invention may be applied in a mixture with the above-named herbicides, or the components of the mixture can be used sequentially. In the case of a sequential treatment, the safening agent may be applied either before or after application of the herbicide. Effective herbicidal amounts of the active ingredients are well understood by those skilled in the art, and such amounts are used together with an effective safening amount of a 3-phenacyl phthalide. The ratio of herbicide to safening agent may vary depending upon the age of the plants at time of treatment, climatic conditions, soil, etc. It is generally preferred, however, to employ a weight ratio of herbicide to safening agent ranging from about 1:10 to 10:1, although ratios of from 1:32 to 32:1 are shown to be effective in the tests below.

Application of the herbicide and safening agent, in admixture or in sequence, may be made directly to the plants or to parts thereof such as stems, leaves, etc. Alternatively, the application can be made to the plant growth medium or to the seeds from which the plants are grown.

The effectiveness of the 3-phenacyl phthalides for the purposes of this invention is demonstrated by the results obtained using the various test procedures hereinafter described. Specific individual compounds employed in these procedures are identified by the numbers they were given in the list of representative compounds, above. Such compounds serve only to illustrate the novel aspects of the invention and should not be construed as a limitation of its scope.

In each test rice, with or without weeds, is grown in a container, and there is an application of the herbicide and a safening agent. In each test there is also a container which receives no application at all, a container to which only the herbicide is applied, and a container to which only the safening agent is applied. The untreated container shows normal plant growth as a standard, and it also serves as an indicator of extraneous conditions which may affect the plants. The other containers show the effect of the herbicide alone, the effect of the safening agent alone, and the effect of the application of both. These effects are in terms of percent inhibition of plant growth relative to the plants in the untreated container.

The "safening effect" is determined by adding the herbicidal effect of the herbicidal when applied alone (A) to the herbicidal effect of the safening agent when applied alone (B) (in no instance, however, will this sum be taken as greater than 100), subtracting from that sum the herbicidal effect obtained when the herbicide and safening agent are both applied (C) to obtain a difference (D), and then calculating the percent reduction of herbicidal effect by said difference by said sum. This is graphically shown below.

$$(A + B) - C = D$$
$$100 \times \frac{D}{A + B} = \text{Safening Effect (\%)}$$

In the following tests all rates of application are shown in kilograms per hectare. An asterisk indicates a safening effect of less than 10%. In those tests where the procedures are replicated, the results represent an average of all replicates.

EXAMPLE 1

A good grade of top soil is placed in a plastic pot and compacted to a depth of approximately 1.27 cm. from the top of said pot. A predetermined number of rice seeds are placed on top of the compacted soil. A quantity of soil sufficient to substantially fill the pot is measured and placed in a second container. A measured quantity of the safening agent dispersed or dissolved in a suitable carrier is applied to the soil in the second container. A measured quantity of the butachlor herbicide dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and butachlor herbicide, and the pot is leveled. The pot is then placed on a sand bench in the greenhouse and watered from below as needed. The plants are observed at the end of approximately 21 days, and the results in terms of percent inhibition of each seed lot are recorded.

The test results which follow will serve to exemplify the reduction in the inhibition of rice plants which is achieved when butachlor herbicide is used in conjunction with a safening agent of this invention.

| Phenacyl Phthalide | Rate | Butachlor Rate | Safening Effect (%) |
|---|---|---|---|
| 1 | 4.48 | 4.48 | 35 |
| 2 | 4.48 | 4.48 | 56 |
| 3 | 4.48 | 4.48 | 66 |
| 4 | 4.48 | 4.48 | 45 |
| 5 | 4.48 | 2.24 | 100 |
| 6 | 2.24 | 2.24 | 25 |
| 7 | 4.48 | 4.48 | 70 |
| 8 | 4.48 | 4.48 | 32 |
| 9 | 8.96 | 4.48 | 64 |
| 10 | 8.96 | 4.48 | 36 |
| 11 | 8.96 | 4.48 | 36 |
| 12 | 8.96 | 4.48 | 36 |
| 13 | 8.96 | 4.48 | 36 |
| 14 | 8.96 | 4.48 | 27 |
| 15 | 8.96 | 4.48 | 34 |
| 16 | 4.48 | 4.48 | 75 |
| 17 | 8.96 | 4.48 | 50 |
| 18 | 8.96 | 4.48 | 63 |
| 19 | 8.96 | 4.48 | 38 |
| 2 | 8.96 | 4.48 | 50 |
| 7 | 8.96 | 4.48 | 44 |
| 20 | 8.96 | 4.48 | 22 |
| 21 | 8.96 | 4.48 | 67 |
| 22 | 8.96 | 4.48 | 47 |
| 2 | 8.96 | 4.48 | 33 |
| 7 | 8.96 | 4.48 | 47 |
| 24 | 8.96 | 4.48 | 40 |
| 2 | 8.96 | 4.48 | 26 |
| 7 | 8.96 | 4.48 | 72 |
| 25 | 8.96 | 4.48 | 26 |
| 26 | 8.96 | 4.48 | 84 |
| 27 | 8.96 | 4.48 | 35 |
| 28 | 8.96 | 4.48 | 29 |
| 29 | 8.96 | 4.48 | 89 |
| 30 | 8.96 | 4.48 | 71 |
| 31 | 8.96 | 4.48 | 71 |
| 32 | 8.96 | 4.48 | 31 |
| 33 | 8.96 | 4.48 | 31 |
| 34 | 8.96 | 4.48 | 42 |
| 35 | 8.96 | 4.48 | 38 |
| 7 | 8.96 | 4.48 | 100 |
| 36 | 8.96 | 6.72 | 23 |
| 37 | 8.96 | 6.72 | 51 |
| 38 | 8.96 | 6.72 | 63 |
| 39 | 8.96 | 6.72 | 67 |
| 40 | 8.96 | 6.72 | 22 |
| 41 | 8.96 | 6.72 | 44 |
| 42 | 8.96 | 6.72 | 44 |
| 43 | 8.96 | 6.72 | 29 |
| 44 | 8.96 | 6.72 | 89 |
| 45 | 8.96 | 6.72 | 47 |
| 47 | 8.96 | 6.72 | * |
| 48 | 8.96 | 4.48 | 75 |

It should be pointed out the test procedures of Example 1 were also carried out with a number of related isomers, homologs and analogs of the 3-phenacyl phthalides of the invention. Many of these related compounds demonstrated little or no safening effect.

EXAMPLE 2

A good grade of top soil is placed in a plastic pot. A measured quantity of the safening agent dispersed or dissolved in a suitable carrier is sprayed on the soil surface. A measured quantity of butachlor herbicide dissolved in a solvent is sprayed on the soil surface. Pre-soaked rice is seeded into the pot which has been flooded with water. The pot is flooded at least up to the soil surface for the duration of the test. The plants are observed at the end of approximately 21 days and the results in terms of percent inhibition of rice are recorded.

The test results which follow will serve to further exemplify the reduction in the inhibition of rice plants which is achieved when butachlor herbicide is used in conjunction with a safening agent of this invention.

| Phenacyl Phthalide | Butachlor Rate | Safening Rate | Effect (%) |
|---|---|---|---|
| 2 | 0.56 | 0.18 | 100 |
|  | 0.56 | 0.07 | 64 |
|  | 0.56 | 0.28 | 20 |
| 2 | 0.035 | 0.0088 | 100 |
|  | 0.035 | 0.035 | 58 |
|  | 0.035 | 0.14 | * |
|  | 0.035 | 0.56 | 10 |
|  | 0.14 | 0.0088 | 83 |
|  | 0.14 | 0.035 | 62 |
|  | 0.14 | 0.14 | 66 |
|  | 0.14 | 0.56 | 26 |
|  | 0.56 | 0.0088 | 100 |
|  | 0.56 | 0.035 | 79 |
|  | 0.56 | 0.14 | 48 |
|  | 0.56 | 0.56 | 45 |
| 3 | 0.56 | 0.018 | 55 |
|  | 0.56 | 0.07 | 55 |
|  | 0.56 | 0.28 | 41 |
| 7 | 1.12 | 0.035 | 100 |
|  | 1.12 | 0.14 | 100 |
|  | 1.12 | 0.56 | 87 |
| 9 | 1.12 | 0.035 | 84 |
|  | 1.12 | 0.14 | 39 |
|  | 1.12 | 0.56 | * |
| 2 | 1.12 | 0.035 | * |
|  | 1.12 | 0.14 | 100 |
|  | 1.12 | 0.56 | 70 |
| 2 | 1.12 | 0.035 | 100 |
|  | 1.12 | 0.14 | 100 |
|  | 1.12 | 0.56 | 84 |
| 16 | 1.12 | 0.035 | * |
|  | 1.12 | 0.14 | 60 |
|  | 1.12 | 0.56 | 55 |
| 17 | 1.12 | 0.035 | * |
|  | 1.12 | 0.14 | 55 |
|  | 1.12 | 0.56 | 52 |
| 18 | 1.12 | 0.035 | 100 |
|  | 1.12 | 0.14 | 14 |
|  | 1.12 | 0.56 | 17 |
| 21 | 1.12 | 0.035 | * |
|  | 1.12 | 0.14 | 55 |
|  | 1.12 | 0.56 | 54 |
| 22 | 1.12 | 0.035 | 31 |
|  | 1.12 | 0.14 | 67 |
|  | 1.12 | 0.56 | 62 |
| 7 | 0.56 | 0.07 | 90 |
|  | 0.56 | 0.28 | 85 |
|  | 0.56 | 1.12 | 10 |
| 26 | 0.56 | 0.07 | 100 |
|  | 0.56 | 0.28 | 75 |
|  | 0.56 | 1.12 | * |
| 27 | 0.56 | 0.07 | 100 |
|  | 0.56 | 0.28 | 75 |
|  | 0.56 | 1.12 | * |
| 1 | 0.56 | 0.07 | * |
|  | 0.56 | 0.28 | * |
|  | 0.56 | 1.12 | * |
| 7 | 0.56 | 0.07 | 100 |
|  | 0.56 | 0.28 | 95 |
|  | 0.56 | 1.12 | 17 |
| 11 | 0.56 | 0.07 | 100 |
|  | 0.56 | 0.28 | 85 |
|  | 0.56 | 1.12 | 20 |
| 13 | 0.56 | 0.07 | 93 |
|  | 0.56 | 0.28 | * |
|  | 0.56 | 1.12 | * |
| 14 | 0.56 | 0.07 | 80 |
|  | 0.56 | 0.28 | 18 |
|  | 0.56 | 1.12 | * |
| 15 | 0.56 | 0.07 | 26 |
|  | 0.56 | 0.28 | * |
|  | 0.56 | 1.12 | * |
| 20 | 0.56 | 0.07 | 22 |
|  | 0.56 | 0.28 | * |
|  | 0.56 | 1.12 | * |

-continued

| Phenacyl Phthalide | Butachlor Rate | Safening Rate | Effect (%) |
| --- | --- | --- | --- |
| 31 | 0.56 | 0.07 | 82 |
|  | 0.56 | 0.28 | 43 |
|  | 0.56 | 1.12 | * |
| 32 | 0.56 | 0.07 | 29 |
|  | 0.56 | 0.28 | * |
|  | 0.56 | 1.12 | * |
| 34 | 0.56 | 0.07 | 41 |
|  | 0.56 | 0.28 | 12 |
|  | 0.56 | 1.12 | * |
| 36 | 0.56 | 0.07 | 82 |
|  | 0.56 | 0.28 | 51 |
|  | 0.56 | 1.12 | * |
| 37 | 0.56 | 0.07 | 83 |
|  | 0.56 | 0.28 | 77 |
|  | 0.56 | 1.12 | 12 |
| 38 | 0.56 | 0.07 | 100 |
|  | 0.56 | 0.28 | 66 |
|  | 0.56 | 1.12 | 12 |
| 39 | 0.56 | 0.07 | 93 |
|  | 0.56 | 0.28 | 95 |
|  | 0.56 | 1.12 | * |
| 40 | 0.56 | 0.07 | 62 |
|  | 0.56 | 0.28 | * |
|  | 0.56 | 1.12 | * |
| 41 | 0.56 | 0.07 | * |
|  | 0.56 | 0.28 | * |
|  | 0.56 | 1.12 | * |
| 47 | 0.56 | 0.07 | 59 |
|  | 0.56 | 0.28 | 23 |
|  | 0.56 | 1.12 | * |
| 48 | 0.56 | 0.07 | 86 |
|  | 0.56 | 0.28 | 85 |
|  | 0.56 | 1.12 | * |
| 7 | 0.56 | 0.07 | 100 |
|  | 0.56 | 0.28 | 94 |
|  | 0.56 | 1.12 | * |
| 29 | 0.56 | 0.07 | 100 |
|  | 0.56 | 0.28 | 35 |
|  | 0.56 | 1.12 | * |
| 31 | 0.56 | 0.07 | 88 |
|  | 0.56 | 0.28 | 36 |
|  | 0.56 | 1.12 | * |
| 37 | 0.56 | 0.07 | 71 |
|  | 0.56 | 0.28 | 79 |
|  | 0.56 | 1.12 | 28 |
| 38 | 0.56 | 0.07 | 63 |
|  | 0.56 | 0.28 | 73 |
|  | 0.56 | 1.12 | 23 |
| 39 | 0.56 | 0.07 | 57 |
|  | 0.56 | 0.28 | 82 |
|  | 0.56 | 1.12 | 30 |
| 41 | 0.56 | 0.07 | 14 |
|  | 0.56 | 0.28 | 12 |
|  | 0.56 | 1.12 | * |
| 46 | 0.56 | 0.07 | 49 |
|  | 0.56 | 0.28 | 31 |
|  | 0.56 | 1.12 | * |
| 48 | 0.56 | 0.07 | 57 |
|  | 0.56 | 0.28 | 76 |
|  | 0.56 | 1.12 | 14 |
| 7 | 0.56 | 0.07 | 81 |
|  | 0.56 | 0.28 | 70 |
|  | 0.56 | 1.12 | 10 |
| 46 | 0.56 | 0.07 | * |
|  | 0.56 | 0.28 | 13 |
|  | 0.56 | 1.12 | * |
| 7 | 0.56 | 0.07 | 90 |
|  | 0.56 | 0.28 | 79 |
|  | 0.56 | 1.12 | 15 |

EXAMPLE 3

A good grade of top soil is placed in a plastic pot. A predetermined number of barnyard grass seeds are applied to the soil surface. A measured quantity of the safening agent dispersed or dissolved in a suitable carrier is sprayed on the soil surface. A measured quantity of butachlor herbicide dissolved in a solvent is sprayed on the soil surface. Pre-soaked rice is seeded into the pot which has been flooded with water. The pot is flooded just above the soil surface for the duration of the test. The plants are observed at the end of approximately 21 days and the results in terms of percent inhibition recorded.

The test results which follow will serve to further exemplify the reduction in the inhibition of rice plants, and also the continued high level of weed control, which is achieved when butachlor herbicide is used in conjunction with a safening agent of this invention.

| Phenacyl Phthalide | Butachlor Rate | Safening Rate | Effect (%) |
| --- | --- | --- | --- |
| 7 | 0.56 | 0.07 | 46 |
|  | 0.56 | 0.28 | 46 |
|  | 0.56 | 1.12 | * |
| 44 | 0.56 | 0.07 | 34 |
|  | 0.56 | 0.28 | * |
|  | 0.56 | 1.12 | * |
| 45 | 0.56 | 0.07 | 15 |
|  | 0.56 | 0.28 | * |
|  | 0.56 | 1.12 | * |

| Phenacyl Phthalide | Rate | Butachlor Rate | Barnyard grass Inhibition (%) |
| --- | --- | --- | --- |
|  |  | 0.07 | 95 |
|  |  | 0.28 | 100 |
|  |  | 1.12 | 100 |
| 7 | 0.56 |  | 0 |
|  | 0.56 | 0.07 | 100 |
|  | 0.56 | 0.28 | 100 |
|  | 0.56 | 1.12 | 100 |
| 44 | 0.56 |  | 0 |
|  | 0.56 | 0.07 | 100 |
|  | 0.56 | 0.28 | 100 |
|  | 0.56 | 1.12 | 100 |
| 45 | 0.56 |  | 0 |
|  | 0.56 | 0.07 | 98 |
|  | 0.56 | 0.28 | 100 |
|  | 0.56 | 1.12 | 100 |

EXAMPLE 4

A good grade of top soil is placed in a plastic pot and compacted to a depth of approximately 1.27 cm. from the top of said pot. A predetermined number of rice seeds and barnyard grass seeds are placed on top of the compacted soil. A quantity of soil sufficient to substantially fill the pot is placed on top of said seeds. A measured quantity of the safening agent dispersed or dissolved in a suitable carrier is sprayed on the soil surface. A measured quantity of the butachlor herbicide dispersed or dissolved in a suitable carrier is then sprayed on the soil surface. The pot is then placed on a sand bench in the greenhouse and watered from below as needed. The plants are observed at the end of approximately 21 days and the results in terms of percent inhibition of each seed lot are recorded.

The test results which follow will serve to further exemplify the reduction in the inhibition of rice plants, and also the continued high level of weed control, which is achieved when butachlor herbicide is used in conjunction with a safening agent of this invention.

| No. 2 Phenacyl Phthalide Rate | Butachlor Rate | Safening Effect (%) |
| --- | --- | --- |
| 0.14 | 2.24 | 28 |

| No. 2 Phenacyl Phthalide Rate | Butachlor Rate | Safening Effect (%) |
|---|---|---|
| 0.14 | 4.48 | 20 |
| 0.14 | 8.96 | * |
| 0.56 | 2.24 | 72 |
| 0.56 | 4.48 | 76 |
| 0.56 | 8.96 | 48 |
| 2.24 | 2.24 | 100 |
| 2.24 | 4.48 | 100 |
| 2.24 | 8.96 | 46 |
| 8.96 | 2.24 | 100 |
| 8.96 | 4.48 | 89 |
| 8.96 | 8.96 | 52 |

This test also included butachlor herbicide at rates of 0.031, 0.14 and 0.56 kilograms per hectare, but the individual data are not included here since the butachlor alone caused no inhibition of rice plants at these rates in this test procedure. With regard to the barnyard grass, butachlor herbicide alone caused 100% inhibition at rates of 2.24, 4.48 and 8.96 kilograms per hectare. The safening agent alone caused no inhibition of barnyard grass at any of the four rates tested. With the twelve rate combinations shown above, there was 100% inhibition of barnyard grass in ten instances. The combination of 8.96 safening agent to 2.24 butachlor gave 90% inhibition, while the combination of 8.96 safening agent to 4.48 butachlor gave 99% inhibition.

EXAMPLE 5

The test procedures described in Example 3 are followed except that the solutions or dispersions of the safening agent and the butachlor herbicide are first mixed together and then sprayed on the soil surface in a single application. The test results are as follows.

| No. 2 Phenacyl Phthalide Rate | Butachlor Rate | Safening Effect (%) | Barnyard Inhibition (%) |
|---|---|---|---|
|  | 0.018 |  | 46 |
|  | 0.07 |  | 94 |
|  | 0.28 |  | 100 |
|  | 1.12 |  | 100 |
| 0.018 | 0.018 | 50 | 58 |
| 0.018 | 0.07 | * | 99 |
| 0.018 | 0.28 | 14 | 100 |
| 0.018 | 1.12 | * | 100 |
| 0.07 | 0.018 | 100 | 63 |
| 0.07 | 0.07 | 56 | 97 |
| 0.07 | 0.28 | 57 | 100 |
| 0.07 | 1.12 | * | 100 |
| 0.28 | 0.018 | 17 | 38 |
| 0.28 | 0.07 | 100 | 90 |
| 0.28 | 0.28 | 54 | 100 |
| 0.28 | 1.12 | * | 100 |
| 1.12 | 0.018 | 100 | 53 |
| 1.12 | 0.07 | 44 | 92 |
| 1.12 | 0.28 | 84 | 100 |
| 1.12 | 1.12 | 50 | 100 |

This test also included butachlor herbicide at a rate of 0.0044 kilograms per hectare, but the individual data are not included here since the butachlor alone caused no inhibition of rice plants at this rate in this test procedure.

| No. 2 Phenacyl Phthalide Rate | Butachlor Rate | Safening Effect (%) | Barnyard Inhibition (%) |
|---|---|---|---|
|  | 0.07 |  | 98 |
|  | 0.28 |  | 100 |
|  | 1.12 |  | 100 |
| 0.07 | 0.07 | 100 | 99 |
| 0.07 | 0.28 | * | 100 |
| 0.07 | 1.12 | * | 100 |
| 0.28 | 0.07 | 100 | 94 |
| 0.28 | 0.28 | 75 | 100 |
| 0.28 | 1.12 | 10 | 100 |
| 1.12 | 0.07 | 100 | 99 |
| 1.12 | 0.28 | 68 | 100 |
| 1.12 | 1.12 | 51 | 100 |
| 0.07 | 0.07 | 100 | 99 |
| 0.07 | 0.28 | 18 | 100 |
| 0.07 | 1.12 | * | 100 |
| 0.28 | 0.07 | 100 | 94 |
| 0.28 | 0.28 | 100 | 100 |
| 0.28 | 1.12 | 26 | 100 |
| 1.12 | 0.07 | 100 | 85 |
| 1.12 | 0.28 | 100 | 100 |
| 1.12 | 1.12 | 95 | 100 |

This test also included butachlor herbicide at a rate of 0.018 kilograms per hectare, but the individual data are not included here since the butachlor alone caused no inhibition of rice plants at this rate in this test procedure.

| Phenacyl Phthalide | Rate | Butachlor Rate | Safening Effect (%) |
|---|---|---|---|
| 2 | 1.12 | 0.07 | 100 |
|  | 1.12 | 0.14 | 100 |
|  | 1.12 | 0.28 | 100 |
|  | 1.12 | 0.56 | 89 |
|  | 1.12 | 1.12 | 74 |
| 7 | 0.07 | 0.07 | 100 |
|  | 0.07 | 0.14 | 85 |
|  | 0.07 | 0.28 | 49 |
|  | 0.07 | 0.56 | * |
|  | 0.07 | 1.12 | * |
|  | 0.28 | 0.07 | 100 |
|  | 0.28 | 0.14 | 91 |
|  | 0.28 | 0.28 | 100 |
|  | 0.28 | 0.56 | 85 |
|  | 0.28 | 1.12 | 23 |
|  | 1.12 | 0.07 | 100 |
|  | 1.12 | 0.14 | 100 |
|  | 1.12 | 0.28 | 100 |
|  | 1.12 | 0.56 | 100 |
|  | 1.12 | 1.12 | 100 |

At each of the five rates in this test, butachlor herbicide alone caused 99% or 100% inhibition of barnyard grass. Every one of the mixtures with a safening agent caused at least 97% inhibition.

EXAMPLE 6

The test procedures described in Example 3 are followed employing each of the active herbicide ingredients named above. The test results are as follows. Herbicide: butachlor

| No. 7 Phenacyl Phthalide Rate | Butachlor Rate | Safening Effect (%) | Barnyard Inhibition (%) |
|---|---|---|---|
|  | 0.07 |  | 89 |
|  | 0.28 |  | 100 |
|  | 1.12 |  | 100 |
| 1.12 | 0.07 | 77 | 93 |
| 1.12 | 0.28 | 100 | 100 |
| 1.12 | 1.12 | 90 | 100 |

This test also included butachlor herbicide at a rate of 0.018 kilograms per hectare, but the individual data are not included here since the butachlor alone caused no inhibition of rice plants at this rate in this test procedure.

Herbicide: 2-chloro-2'-tert. butyl-6'-methylacetanilide

| No. 7 Phenacyl Phthalide Rate | Herbicide Rate | Safening Effect (%) | Barnyard Inhibition (%) |
|---|---|---|---|
|  | 0.018 |  | 80 |
|  | 0.07 |  | 99 |
|  | 0.28 |  | 100 |
|  | 1.12 |  | 100 |
| 1.12 | 0.018 | 100 | 80 |
| 1.12 | 0.07 | 48 | 99 |
| 1.12 | 0.28 | * | 100 |
| 1.12 | 1.12 | * | 100 |

Herbicide: N-(2-butoxyethyl)-N-(2,6-dimethyl-1-cyclohexen-1-yl)-α-chloroacetamide

| No. 7 Phenacyl Phthalide Rate | Herbicide Rate | Safening Effect (%) | Barnyard Inhibition (%) |
|---|---|---|---|
|  | 0.018 |  | 93 |
|  | 0.07 |  | 99 |
|  | 0.28 |  | 100 |
|  | 1.12 |  | 100 |
| 1.12 | 0.018 | 100 | 98 |
| 1.12 | 0.07 | 100 | 100 |
| 1.12 | 0.28 | 34 | 100 |
| 1.12 | 1.12 | * | 100 |

Herbicide: 2-chloro-2'-tert. butyl-6'-methyl-N-(butoxymethyl)acetanilide

| No. 7 Phenacyl Phthalide Rate | Herbicide Rate | Safening Effect (%) | Barnyard Inhibition (%) |
|---|---|---|---|
|  | 0.07 |  | 99 |
|  | 0.28 |  | 100 |
|  | 1.12 |  | 100 |
| 1.12 | 0.07 | 91 | 100 |
| 1.12 | 0.28 | * | 100 |
| 1.12 | 1.12 | * | 100 |

This last test also included the herbicide at a rate of 0.018 kilograms per hectare, but the individual data are not included here since the herbicide alone caused no inhibition of rice plants at this rate in this test procedure.

Herbicide: molinate

| No. 7 Phenacyl Phthalide Rate | Molinate Rate | Safening Effect (%) | Barnyard Inhibition (%) |
|---|---|---|---|
|  | 4.48 |  | 100 |
| 2.24 | 4.48 | 100 | 100 |

Herbicide: benthiocarb

| No. 7 Phenacyl Phthalide Rate | Benthiocarb Rate | Safening Effect (%) | Barnyard Inhibition (%) |
|---|---|---|---|
|  | 1.12 |  | 99 |
|  | 4.48 |  | 100 |
| 2.24 | 1.12 | 88 | 100 |
| 2.24 | 4.48 | 12 | 100 |

Herbicide: butralin

| No. 7 Phenacyl Phthalide Rate | Butralin Rate | Safening Effect (%) | Barnyard Inhibition (%) |
|---|---|---|---|
|  | 0.14 |  | 93 |
|  | 0.56 |  | 100 |
|  | 2.24 |  | 100 |
| 2.24 | 0.14 | 100 | 38 |
| 2.24 | 0.56 | 78 | 98 |
| 2.24 | 2.24 | * | 100 |

The last three tests also included molinate at rates of 0.07, 0.28 and 1.12 kilograms per hectare, benthiocarb at rates of 0.07 and 0.28 kilograms per hectare and butralin at a rate of 0.035 kilograms per hectare. The individual data are not included here since each herbicide alone caused no inhibition of rice plants at the stated rates in this test procedure. It should also be noted that the safener alone at the rate of 2.24 kilograms per hectare caused 23% inhibition of the barnyard grass.

EXAMPLE 7

A good grade of top soil is placed in a pan and compacted to a depth of approximately 1.27 cm. from the top of the pan. A predetermined number of seeds of six species of weeds, and a predetermined number of rice seeds, are placed on top of the compacted soil. A quantity of soil sufficient to substantially fill the pan is placed on top of said seeds. A mixture of the solutions or dispersions of the safening agent and the butachlor herbicide is prepared and sprayed on the soil surface in a single application. The pan is then sprayed with water, placed on a sand bench, and watered from below as needed. The plants are observed at the end of approximately 21 days, and the results in terms of percent inhibition of each seed lot are recorded.

The weed species employed in this test are redroot pigweed (PW), green foxtail (FT), crabgrass (CG), panicum (proso millet) (PAN), barnyard grass (BG) and wild oats (WO). The herbicidal effect on these weeds, and the safening effect on rice, are as follows.

| No. 7 Phenacyl Phthalide Rate | Butachlor Rate | Weed Inhibition (%) | | | | | | Safening Effect (%) |
|---|---|---|---|---|---|---|---|---|
|  |  | PW | FT | CG | PAN | BG | WO |  |
|  | 0.07 | 95 | 77 | 85 | 77 | 93 | 23 |  |
|  | 0.56 | 100 | 100 | 97 | 95 | 100 | 75 |  |
|  | 4.48 | 100 | 100 | 100 | 100 | 100 | 90 |  |
| 0.07 | 0.07 | 90 | 90 | 87 | 55 | 95 | 0 |  |
| 0.07 | 0.56 | 95 | 97 | 91 | 90 | 100 | 70 | * |
| 0.07 | 4.48 | 100 | 100 | 100 | 100 | 100 | 93 | 22 |
| 0.56 | 0.07 | 70 | 93 | 85 | 43 | 93 | 0 |  |
| 0.56 | 0.56 | 95 | 99 | 95 | 90 | 99 | 50 | 40 |
| 0.56 | 4.48 | 100 | 99 | 99 | 99 | 100 | 90 | 38 |
| 4.48 | 0.07 | 67 | 87 | 83 | 27 | 87 | 5 |  |
| 4.48 | 0.56 | 99 | 99 | 90 | 82 | 99 | 25 | 100 |

-continued

| No. 7 Phenacyl Phthalide Rate | Butachlor Rate | Weed Inhibition (%) | | | | | | Safening Effect (%) |
|---|---|---|---|---|---|---|---|---|
| | | PW | FT | CG | PAN | BG | WO | |
| 4.48 | 4.48 | 100 | 100 | 100 | 95 | 100 | 77 | 100 |

In this test the safening agent alone showed no effect on any of the weed species or on the rice at the three application rates. No safening effect data is shown for combinations with the butachlor herbicide at the 0.07 rate since the herbicide alone showed no effect on the rice at that rate in this test procedure.

EXAMPLE 8

Dichloromethane solutions containing various concentrations of a safening agent of this invention are prepared and used to treat rice seeds. The treated seeds are then pregerminated for 2 days on moist towels. A plastic pot is partially filled with a good grade of top soil. Barnyard grass is seeded into the soil, after which the pot is filled with additional soil, and butachlor herbicide dissolved in a solvent is sprayed on the soil surface. The pot is flooded and seeded with the pregerminated rice. The water level is lowered to the soil surface after 24 hours, and it is held at or below this level for 5-7 days. The pot is then reflooded for the duration of the test, and observations are made at the end of approximately 21 days.

The results which follow show that seed treatment with a safening agent will serve to reduce the inhibition of rice plants while the high level of weed control is maintained. The application rate for the safening agent is given in terms of grams of safening agent per kilogram of seed weight.

| No. 7 Phenacyl Phthalide Rate | Butachlor Rate | Safening Effect (%) | Barnyard Inhibition (%) |
|---|---|---|---|
| | 0.018 | | 89 |
| | 0.07 | | 97 |
| | 0.28 | | 100 |
| | 1.12 | | 100 |
| 0.31 | 0.018 | 38 | 78 |
| 0.31 | 0.07 | 100 | 99 |
| 0.31 | 0.28 | 64 | 100 |
| 0.31 | 1.12 | 15 | 100 |
| 1.25 | 0.018 | 100 | 90 |
| 1.25 | 0.07 | 82 | 93 |
| 1.25 | 0.28 | 86 | 100 |
| 1.25 | 1.12 | 62 | 100 |
| 5.0 | 0.018 | 100 | 88 |
| 5.0 | 0.07 | 100 | 99 |
| 5.0 | 0.28 | 100 | 100 |
| 5.0 | 1.12 | 70 | 100 |

In this test the safening agent alone showed no effect on the barnyard grass or on the rice at any of the three application rates.

Although most of the preceding examples show the use of the described test procedures with more than one safening agent of this invention, it should be understood that all of the tests within a single example were not necessarily conducted at the same time. However, it should also be understood, that an untreated container, plus containers with the herbicide alone and the safening agent alone, are employed for each test initiation date. These are the controls used to obtain the herbicide and safening effect data for tests begun on that particular date.

From the standpoint of safening effectiveness coupled with continued high inhibition of weeds, it is preferred to employ those compounds of this invention wherein a is zero, Q is hydrogen and R is selected from 2'-chloro or 2'-methoxyphenyl, 2'-methoxy-5'-methylphenyl, and 2',5'-dimethyl, dimethoxy or diethylphenyl. Within this group, the most especially preferred members are those wherein the substitution on the phenyl ring is either 2'-chloro or 2',5'-dimethoxy.

The herbicide, safening agent or mixture thereof may be applied to the plant or plant growth medium alone, or the herbicide, safening agent or mixture thereof may be applied in conjunction with a material referred to in the art as an adjuvant in liquid or solid form. Mixtures containing the herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant or plant growth medium, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention can be accomplished by incorporating the compositions in the soil or other media.

Example 8 also illustrates that the rice plants may be protected by treating the rice seed with an effective amount of safening agent prior to planting. Generally, small amounts of safening agent are required to treat such seeds. Said example demonstrates that a weight ratio of as little as 0.3 parts of safener per 1000 parts of seed may be effective. The amount of safener utilized in treating the seed may be increased if desired. Generally, however, a weight ratio of safening agent to seed weight may range from 0.1 to 10.0 parts of safening agent per 1000 parts of seed. The determination of the effective amount of safening agent required is well within the skill of the art.

Since only a very small amount of active safening agent is usually required for the seed treatment, it is preferably formulated as a powder or an emulsifiable concentrate which can be diluted with water by the seed treater for use in a seed treating apparatus. Of course, under certain conditions, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkalicasein compositions, long chain alcohols usually containing 10–18 carbon atoms, and condensation products of ethylene oxide with fatty acids, alkylphenols and mercaptans.

While the invention has been described herein with regard to certain representative examples for purpose of illustrating its practice, it is not to be construed as limited thereto. Those skilled in the art will readily recognize the variations and modifications which can be made without departing from the spirit and scope of the invention.

What is claimed is:

1. A method of reducing injury to rice plants due to application thereto of a herbicide selected from the group consisting of butachlor, 2-chloro-2'-tert. butyl-6'-methylacetanilide, N-(2-butoxyethyl)-N-(2,6-dimethyl-1-cyclohexen-1-yl)-α-chloroacetamide and 2-chloro-2'-tert. butyl-6'-methyl-N-(butoxymethyl)acetanilide which comprises applying to said rice plants or to the plant growth medium an effective safening amount of a compound of the formula

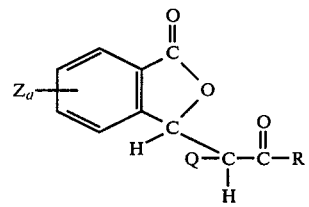

wherein: R is selected from phenyl, α-naphthyl, cyclohexyl, dichlorophenyl provided that the chloro substituents are not on adjacent carbon atoms, trichlorophenyl, di(lower alkyl)phenyl, tri(lower alkyl)phenyl, di(lower alkoxy) phenyl provided that at least one meta position is unsubstituted,

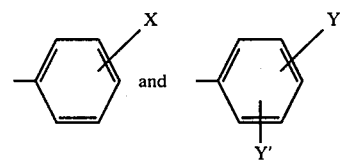

where X is lower alkyl, lower alkoxy, chloro, fluoro, iodo, trifluoromethyl, hydroxy, amino or 3'-nitro, and Y and Y' are unlike and are hydroxy, methyl or lower alkoxy; a is zero or one; Z is selected from 5, 6 or 7-chloro, 6-nitro and methoxy provided that when Z is 4-methoxy R must be a substituted phenyl; and Q is hydrogen or bromo provided that when Q is bromo at least one of X, Y, Y' or Z must be lower alkoxy.

2. A method as defined in claim 1 wherein a is zero and Q is hydrogen.

3. A method as defined in claim 2 wherein R is 2'-chloro or 2'-methoxyphenyl.

4. A method as defined in claim 3 wherein R is 2'-chlorophenyl.

5. A method as defined in claim 3 wherein R is 2'-methoxyphenyl.

6. A method as defined in claim 2 wherein R is selected from 2'-methoxy-5'-methylphenyl and 2',5'-dimethyl, 2',5'-diethyl or 2',5'-dimethoxyphenyl.

7. A method as defined in claim 6 wherein R is 2'-methoxy-5'-methylphenyl.

8. A method as defined in claim 6 wherein R is 2',5'-dimethylphenyl.

9. A method as defined in claim 6 wherein R is 2',5'-diethylphenyl.

10. A method as defined in claim 6 wherein R is 2',5'-dimethoxyphenyl.

11. A method as defined in claim 1 wherein the weight ratio of said herbicide to said compound is from 1:32 to 32:1.

12. A method as defined in claim 1 wherein the weight ratio of said herbicide to said compound is from 1:10 to 10:1.

13. A method as defined in claim 3 wherein said herbicide is butachlor.

14. A method as defined in claim 6 wherein said herbicide is butachlor.

15. A method of reducing herbicidal injury to rice plants which comprises applying to said rice plants or to the plant growth medium an effective amount of a mixture comprising a herbicidally effective amount of a herbicide selected from the group consisting of butachlor, 2-chloro-2'-tert. butyl-6'-methylacetanilide, N-(2-butoxyethyl)-N-(2,6-dimethyl-1-cyclohexen-1-yl)-α-chloroacetamide and 2-chloro-2'-tert. butyl-6'-methyl-N-(butoxymethyl)acetanilide and an effective safening amount of a compound of the formula

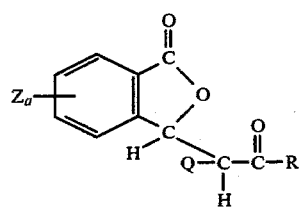

wherein: R is selected from phenyl, α-naphthyl, cyclohexyl, dichlorophenyl provided that the chloro substituents are not on adjacent carbon atoms, trichlorophenyl, di(lower alkyl)phenyl, tri(lower alkyl)phenyl, di(lower alkoxy) phenyl provided that at least one meta position is unsubstituted,

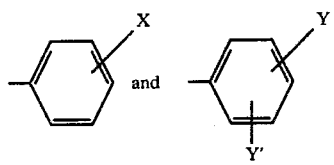

where X is lower alkyl, lower alkoxy, chloro, fluoro, iodo, trifluoromethyl, hydroxy, amino or 3'-nitro, and Y and Y' are unlike and are hydroxy, methyl or lower alkoxy; a is zero or one; Z is selected from 5, 6 or 7-chloro, 6-nitro and methoxy provided that when Z is 4-methoxy R must be a substituted phenyl; and Q is hydrogen or bromo provided that when Q is bromo at least one of X, Y, Y' or Z must be lower alkoxy.

16. A method as defined in claim 15 wherein a is zero and Q is hydrogen.

17. A method as defined in claim 16 wherein R is 2'-chloro or 2'-methoxyphenyl.

18. A method as defined in claim 17 wherein R is 2'-chlorophenyl.

19. A method as defined in claim 17 wherein R is 2'-methoxyphenyl.

20. A method as defined in claim 16 wherein R is selected from 2'-methoxy-5'-methylphenyl and 2',5'-dimethyl, 2',5'-diethyl or 2',5'-dimethoxyphenyl.

21. A method as defined in claim 20 wherein R is 2'-methoxy-5'-methylphenyl.

22. A method as defined in claim 20 wherein R is 2',5'-dimethylphenyl.

23. A method as defined in claim 20 wherein R is 2',5'-diethylphenyl.

24. A method as defined in claim 20 wherein R is 2',5'-dimethoxyphenyl.

25. A method as defined in claim 15 wherein the weight ratio of said herbicide to said compound is from 1:32 to 32:1.

26. A method as defined in claim 15 wherein the weight ratio of said herbicide to said compound is from 1:10 to 10:1.

27. A method as defined in claim 17 wherein said herbicide is butachlor.

28. A method as defined in claim 20 wherein said herbicide is butachlor.

29. A method of reducing injury to rice plants due to application thereto of a herbicide selected from the group consisting of butachlor, 2-chloro-2'-tert. butyl-6'-methylacetanilide, N-(2-butoxyethyl)-N-(2,6-dimethyl-1-cyclohexen-1-yl)-α-chloroacetamide and 2-chloro-2'-tert. butyl-6'-methyl-N-(butoxymethyl)acetanilide which comprises applying to the seeds from which said rice plants are grown a safening effective amount of a compound of the formula

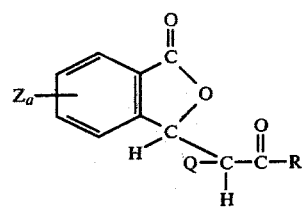

wherein: R is selected from phenyl, α-naphthyl, cyclohexyl, dichlorophenyl provided that the chloro substituents are not on adjacent carbon atoms, trichlorophenyl, di(lower alkyl)phenyl, tri(lower alkyl)phenyl, di(lower alkoxy)phenyl provided that at least one meta position is unsubstituted,

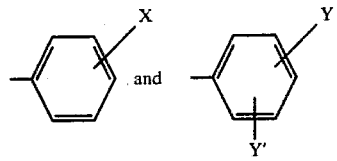

where X is lower alkyl, lower alkoxy, chloro, fluoro, iodo, trifluoromethyl, hydroxy, amino or 3'-nitro, and Y and Y' are unlike and are hydroxy, methyl or lower alkoxy; a is zero or one; Z is selected from 5, 6 or 7-chloro, 6-nitro and methoxy provided that when Z is 4-methoxy R must be a substituted phenyl; and Q is hydrogen or bromo provided that when Q is bromo at least one of X, Y, Y' or Z must be lower alkoxy.

30. A method as defined in claim 29 wherein a is zero and Q is hydrogen.

31. A method as defined in claim 30 wherein R is 2'-chloro or 2'-methoxyphenyl.

32. A method as defined in claim 31 wherein R is 2'-chlorophenyl.

33. A method as defined in claim 31 wherein R is 2'-methoxyphenyl.

34. A method as defined in claim 30 wherein R is selected from 2'-methoxy-5'-methylphenyl and 2',5'-dimethyl, 2',5'-diethyl or 2',5'-dimethoxyphenyl.

35. A method as defined in claim 34 wherein R is 2'-methoxy-5'-methylphenyl.

36. A method as defined in claim 34 wherein R is 2',5'-dimethylphenyl.

37. A method as defined in claim 34 wherein R is 2',5'-diethylphenyl.

38. A method as defined in claim 34 wherein R is 2',5'-dimethoxyphenyl.

39. A method as defined in claim 29 wherein said compound is applied in a weight ratio of from 0.1 to 10.0 parts of compound per 1000 parts of seed.

40. A method as defined in claim 31 wherein said herbicide is butachlor.

41. A method as defined in claim 34 wherein said herbicide is butachlor.

42. A mixture which comprises a herbicidally effective amount of a herbicide selected from the group consisting of butachlor, 2-chloro-2'-tert. butyl-6'-methylacetanilide, N-(2-butoxyethyl)-N-(2,6-dimethyl-1-cyclohexen-1-yl)-α-chloroacetamide and 2-chloro-2'-tert. butyl-6'-methyl-N-(butoxymethyl)acetanilide and an effective safening amount of a compound of the formula

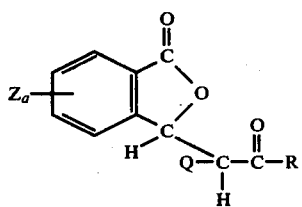

wherein: R is selected from phenyl, α-naphthyl, cyclohexyl, dichlorophenyl provided that the chloro substituents are not on adjacent carbon atoms, trichlorophenyl, di(lower alkyl)phenyl, tri(lower alkyl)phenyl, di(lower alkoxy) phenyl provided that at least one meta position is unsubstituted,

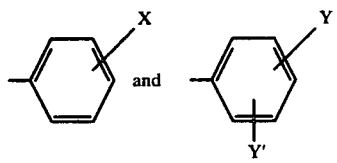

where X is lower alkyl, lower alkoxy, chloro, fluoro, iodo, trifluoromethyl, hydroxy, amino or 3'-nitro, and Y and Y' are unlike and are hydroxy, methyl or lower alkoxy; a is zero or one; Z is selected from 5, 6 or 7-chloro, 6-nitro and methoxy provided that when Z is 4-methoxy R must be a substituted phenyl; and Q is hydrogen or bromo provided that when Q is bromo at least one of X, Y, Y' or Z must be lower alkoxy.

43. A mixture as defined in claim 42 wherein a is zero and Q is hydrogen.

44. A mixture as defined in claim 43 wherein R is 2'-chloro or 2'-methoxyphenyl.

45. A mixture as defined in claim 44 wherein R is 2'-chlorophenyl.

46. A mixture as defined in claim 44 wherein R is 2'-methoxyphenyl.

47. A mixture as defined in claim 43 wherein R is selected from 2'-methoxy-5'-methylphenyl and 2',5'-dimethyl, 2',5'-diethyl or 2',5'-dimethoxyphenyl.

48. A mixture as defined in claim 47 wherein R is 2'-methoxy-5'-methylphenyl.

49. A mixture as defined in claim 47 wherein R is 2',5'-dimethylphenyl.

50. A mixture as defined in claim 47 wherein R is 2',5'-diethylphenyl.

51. A mixture as defined in claim 47 wherein R is 2',5'-dimethoxyphenyl.

52. A mixture as defined in claim 42 wherein the weight ratio of said herbicide to said compound is from 1:32 to 32:1.

53. A mixture as defined in claim 42 wherein the weight ratio of said herbicide to said compound is from 1:10 to 10:1.

54. A mixture as defined in claim 44 wherein said herbicide is butachlor.

55. A mixture as defined in claim 47 wherein said herbicide is butachlor.

* * * * *